United States Patent
Zaharik et al.

(10) Patent No.: US 11,011,278 B1
(45) Date of Patent: May 18, 2021

(54) METHODS AND RAPID TEST KITS FACILITATING EPIDEMIOLOGICAL SURVEILLANCE

(71) Applicant: bioLytical Laboratories Inc., Richmond (CA)

(72) Inventors: Michelle L Zaharik, Vancouver (CA); Ron P Heyde, Richmond (CA)

(73) Assignee: bioLytical Laboratories Inc., Richmond (CA)

(*) Notice: Subject to any disclaimer, the term of this patent is extended or adjusted under 35 U.S.C. 154(b) by 0 days.

(21) Appl. No.: 17/026,643

(22) Filed: Sep. 21, 2020

(51) Int. Cl.
| | |
|---|---|
| *G16H 50/80* | (2018.01) |
| *G01N 33/543* | (2006.01) |
| *B01L 3/00* | (2006.01) |
| *G16H 40/67* | (2018.01) |
| *G06K 19/06* | (2006.01) |

(52) U.S. Cl.
CPC ............ *G16H 50/80* (2018.01); *B01L 3/5023* (2013.01); *G01N 33/54366* (2013.01); *G16H 40/67* (2018.01); *B01L 2300/021* (2013.01); *B01L 2300/023* (2013.01); *G06K 19/06028* (2013.01); *G06K 19/06037* (2013.01)

(58) Field of Classification Search
CPC .. G16H 50/80; G16H 40/67; G01N 33/54366; B01L 3/5023; B01L 2300/021; B01L 2300/023; G06K 19/06028; G06K 19/06037
See application file for complete search history.

(56) References Cited

U.S. PATENT DOCUMENTS

| | | | |
|---|---|---|---|
| 4,510,383 | A | 4/1985 | Puppender |
| 4,592,893 | A | 6/1986 | Poppe |
| 6,770,487 | B2 | 8/2004 | Crosby |
| 7,270,970 | B2 | 9/2007 | Anderson |
| 8,715,590 | B2 | 5/2014 | Cohen |
| 8,862,448 | B2 | 10/2014 | Holmes |
| 9,335,290 | B2 | 5/2016 | Ewart |

(Continued)

FOREIGN PATENT DOCUMENTS

| | | | | |
|---|---|---|---|---|
| WO | WO 2008/104081 | | 9/2008 | |
| WO | WO-2008104081 | A1 * | 9/2008 | ....... G01N 33/56988 |
| WO | WO 2009/061514 | | 5/2009 | |

OTHER PUBLICATIONS

Feng et al, "Immunochromatographic Diagnostic Test Analysis Using Google Glass" ACS Nano 2014 vol. 8, No. 3, pp. 3069-3079 (Year: 2014).*

(Continued)

*Primary Examiner* — Dennis White
(74) *Attorney, Agent, or Firm* — Boris Leschinsky (57) ABSTRACT

A method for facilitating epidemiologic surveillance for a target disease such as Covid-19 includes a step of using an optical identifier such as a barcode or a numerical code to rapidly report de-identified test results to a central database. A rapid test device may be based on a direct flow point-of-care device comprising a porous membrane with at least one recombinant antigen applied thereto and procedural control. The recombinant antigen may comprise an epitope for detecting the target disease marker. The first optical identifier may be applied to the device and facilitate remote communication of the test results without the use of any specialized equipment.

26 Claims, 2 Drawing Sheets

(56) References Cited

U.S. PATENT DOCUMENTS

| | | | |
|---|---|---|---|
| 9,439,630 | B2 | 9/2016 | Zimmerle |
| 10,541,056 | B2 | 1/2020 | Booker |
| 10,887,104 | B1* | 1/2021 | Jayachandran ....... H04L 9/3218 |
| 2003/0165970 | A1* | 9/2003 | Hu ..................... G01N 33/5761 |
| | | | 435/6.16 |
| 2010/0267049 | A1 | 10/2010 | Rutter |
| 2013/0230845 | A1 | 9/2013 | Egan |
| 2017/0234867 | A1 | 8/2017 | Anderberg |
| 2019/0187139 | A1 | 6/2019 | Xie |
| 2019/0194484 | A1* | 6/2019 | Villwock ............. C09D 11/328 |

OTHER PUBLICATIONS

BD Veritor System (Aug. 2020) pp. 1-17 (Year: 2020).*

"Navica™ Mobile App and Binaxnow™ COVID-19 Ag CARD" www.globalpointofcare.abbott/en/product-details/navica-binaxnow-covid-19-US.html captured on wayback machine on Aug. 28, 2020 p. 1-7 (Year: 2020).*

"BinaxNOW™ COVID-19 Ag CARD" https://www.fda.gov/media/141570/download captured on wayback machine on Aug. 27, 2020 p. 1-17 (Year: 2020).*

Scherr TF, Gupta S, Wright DW, Haselton FR. An embedded barcode for "connected" malaria rapid diagnostic tests. Lab Chip. Mar. 29, 2017; 17(7): 1314-1322.

* cited by examiner

METHODS AND RAPID TEST KITS FACILITATING EPIDEMIOLOGICAL SURVEILLANCE

BACKGROUND

Without limiting the scope of the invention, its background is described in connection with epidemiological surveillance of a target disease that may affect large masses of population and spread over significant geographical areas. More particularly, the invention describes methods for facilitating the collection of an extensive number of individual test results using rapid test kits and commonly available communication means.

An epidemic of an infectious disease capable of spreading across a large region, across continents or throughout the entire world, can be hugely costly to societies. Such incidences in the past included pandemics of influenza, smallpox, tuberculosis, human immune deficiency virus (HIV), and Severe Acute Respiratory Syndrome (SARS). More recently, an ongoing worldwide pandemic of Covid-19 (also referred to in this description as Coronavirus or SARS-CoV-2) already caused an infection in tens of millions of people and close to one million deaths. Direct healthcare costs and economic losses of this pandemic are incalculable.

While the world awaits an effective vaccine and methods of treatment, conventional mitigation methods are used to limit the spread of the disease including wearing a face mask and maintaining a social distance. Widespread testing of large populations in many regions of the world is instrumental in monitoring the disease prevalence and allowing for better allocation of healthcare and other resources.

Accurate and timely knowledge of the extent of disease spread as well as the extent of immunity afforded by natural or vaccine-induced disease-specific antibodies is highly sought after by government organizations in charge of public health. Such knowledge is also important to convince the public to not engage in "avoidance behavior", which leads to a substantial reduction of economic activity leading to further exacerbation of direct economic losses caused by the disease. World Bank estimates that "avoidance behavior" causes as much as five times the economic damage compared with direct healthcare costs and absence at work by those affected by the disease.

Rapid Point-Of-Care (POC) tests allow rapid diagnostics to be performed by a patient or a healthcare professional at the bedside or elsewhere near the patient, including at home, a pharmacy, or a clinic where the test is made available. Using these tests increases the likelihood that the patient, physician, and care team will receive the results quicker, which allows for better immediate clinical management decisions to be made.

Many POC tests are realized as easy-to-use membrane-based test strips, often enclosed in a plastic test cartridge. This concept is often realized in test systems for detecting various pathogens. The most commonly used membrane-based POC tests are so-called "lateral flow" tests, which can produce a visual indicator of a presence or absence of a target disease in a manner of 15-20 minutes. A great number of such tests to detect a variety of diseases are produced by a long list of manufacturers and are routinely used by many laboratories, as well as directly by individuals. An improved POC test that replaces lateral flow with direct flow and provides accurate test results in under 5 minutes is the INSTI® rapid test for HIV-1/HIV-2 manufactured by bioLytical Laboratories Inc. (Richmond, Canada), the assignee of the present invention.

Test results from a POC cartridge are often presented to the user as a visual indicator. Although easy to understand when it comes to an individual test, a visual indicator methodology is not trivial to accurately record each test result and communicate to a large number of patients when it comes to mass testing of people for epidemiologic surveillance.

As explained by the Centers for Disease Control and Prevention (CDC), Electronic Laboratory Reporting (ELR) is the automated transmission of laboratory-related data from commercial, public health, hospital, and other labs to state and local public health departments through an electronic health records (EHR) system or a Laboratory Information Management System (LIMS). ELR helps identify reportable conditions determined by confirmatory testing and supports case reporting at the state or local level. ELR is used by laboratory providers to help them meet state laws on reportable diseases mandating that providers report cases of specified diseases to the health department. ELR supports overall public health surveillance by helping improve the timeliness and accuracy of case reporting and confirmation to state and local health departments. It also supports national public health surveillance by improving the timeliness and accuracy of notifiable disease data voluntarily shared by states with CDC.

This methodology works well in the US, EU, and other developed countries having similar systems in place. However, these centralized health surveillance systems may not be readily available or even easily accessible in many developing countries. Moreover, even in developed countries, such systems may not account for tests performed individually at home or elsewhere outside a traditional laboratory. This may lead to a substantial underestimate of the spread of the target disease.

An additional complication for large scale health surveillance is the requirement to ensure privacy of individual patient diagnostic results. Many prior art laboratory systems and sample labeling processes have been designed to track individual patient samples, for the sake of accurate correlation of the test result with the correct individual. However, these tracking systems also permit health data of individual subjects to be easily shared which creates privacy concerns that compromise their utility in health surveillance systems. Subjects would be more motivated to participate in large scale health surveillance if they could be guaranteed an anonymous reporting system that is simple, quick and effective, yet still obtain a diagnostic result privately.

The need exists therefore for new methods and test kits adapted to facilitate health surveillance reporting to include the maximum number of reported tests performed for diagnosing a target disease throughout various economic conditions and test application circumstances. A massive enhancement of health surveillance testing for use in areas of the world with less access to data technology is especially needed to address the Covid-19 pandemic.

SUMMARY

Accordingly, it is an object of the present invention to overcome these and other drawbacks of the prior art by providing novel methods and rapid test kits for epidemiological surveillance of the target disease, wherein such rapid test kits are configured for easy reporting of test results by both clinicians as well as individual patients.

It is another object of the present invention to provide novel methods and rapid test kits for epidemiological surveillance of the target disease, wherein such rapid test kits are configured to facilitate remote communication of test results by a variety of long-distance communication means such as telephone lines, cellular networks, and the Internet.

It is a further object of the present invention to provide novel universal rapid test kits for epidemiological surveillance of the target disease, wherein each test kit comprises a plurality of individual rapid test devices, such that both the test kit as well as individual rapid test devices may be used independently to facilitate remote communication of test results to a central database—regardless of whether these rapid tests are performed in batches by a clinician or individually by patients themselves.

It is yet a further object of the present invention to provide novel methods and rapid test kits for epidemiological surveillance of the target disease, wherein such rapid test kits are universally applicable worldwide for use in a variety of regions with a broad spectrum of economic development and availability of modem communication networks.

The rapid test kit of the present invention may include at least one or more of rapid test devices. Each of the rapid test devices in turn may include a housing containing a porous membrane facing the user and a procedural control applied thereto. The procedural control may be configured to generate a first visual indicator to confirm the validity of the test procedure—for example, a blue dot in a designated area of the porous membrane, which is visible to the user.

Each rapid test may further contain one or more recombinant antigens, each of the recombinant antigens comprising at least one epitope specific for a disease marker corresponding to the target disease. All of the recombinant antigens may be applied to the porous membrane in individually-designated areas so as to capture human generated antibodies specific to the target disease marker. Applying a single collected fluid specimen in this case to the porous membrane will result in the activation of the procedural control as well as one or more recombinant antigens. The recombinant antigens may be configured to form at least one or more second visual indicators (such as, for example, a change of their color) adapted to visually confirm if the disease marker is present in the collected specimen.

Importantly, the rapid test kit may further include a first optical identifier such as a barcode or a numeric code applied to either the rapid test kit and/or each of the rapid test devices. The first optical identifier may be configured to include information about the specific type of test to be performed using the rapid test device as well as additional test-related information. In embodiments, the first optical identifier may also include a portion of the optical code to lead the user to a dedicated website of the central database, or to a location from which the user may download a dedicated smartphone or computer software application configured to facilitate a secure remote transmission of test results to the central database.

The first optical identifier may comprise a pair of individual optical identifiers, one for use by the user to remotely communicate a positive test result and the other to be used for remotely communicate a negative test result.

In embodiments, a novel method of epidemiological surveillance may include the steps of:
a. providing a rapid test kit as described above,
b. collecting the single fluid specimen from a subject and applying the single specimen to the porous membrane,
c. visually confirming rapid test validity using the first visual indicator change in color,
d. visually detecting a test result using the second visual indicator including a presence (defining a positive test result) or an absence (defining a negative test result) of the target disease marker in the subject, and
e. after performing the rapid test, using the first optical identifier to remotely communicate the test result to a central database configured for epidemiological surveillance of the target disease, wherein the remote communicating further permits identifying a time of the rapid test and a location of the rapid test.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through the use of the accompanying drawings, in which:

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Rapid Test Device

Figure 1:
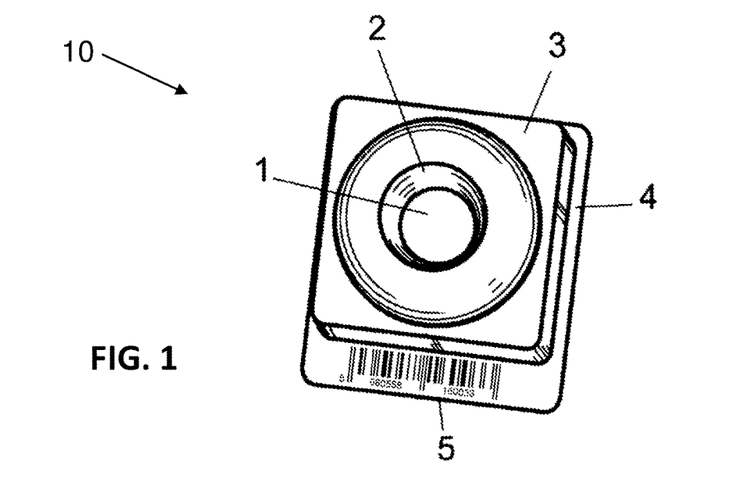
FIG. 1 is a perspective view of an individual rapid test device of the present invention.

FIG. 1 shows a general perspective view of an exemplary rapid test device 10 with a housing 4 featuring a well-shaped receptacle 2 in which a single fluid specimen collected from a subject can be poured along with complementary buffers and reagents if needed. The rapid test device 10 further features a porous membrane 1 located immediately at the bottom of the well of the receptacle 2. The porous membrane 1 may comprise an immobilized procedural control and one or more recombinant antigens of different combinations of epitopes of the target disease markers. The rapid test device 10 may include a reservoir 3 containing an absorbent material configured to collect and retain fluids that are flown through the porous membrane 1 during the test. The absorbent material may further be configured to support the membrane 1 in its position during the application of one or more fluids of the test procedure.

Further details of the rapid test device 10 may be found in the WO 2008/104081 document, which is incorporated herein by reference in its entirety. In particular, the document describes positioning one or more recombinant antigens in various individually designated areas of the porous membrane 1 forming dots in various quadrants thereof. Initially, the entire porous membrane 1 is visible to the user in a single color, such as white. As test fluids are added to the rapid test device 10 and flow through the porous membrane 1, one or more of the dots may change its color to that which contrasts with the original color of the porous membrane. In one example, one or more of the procedural control and/or recombinant antigen locations may turn blue, which becomes visible to the user within a short period of time, typically within about 1 minute. Additional details on the INSTI™ HIV-1/HIV-2 Antibody Test Kit may be found on the Package Insert provide with the kit and available at https/www.fda.gov/media/79719/download (last accessed: 14 Sep. 2020).

A POC test device, and kits comprising multiple devices, in one embodiment, are provided with all the components needed for the user to self-execute the test. One exemplary device includes a finger prick tool, a capillary tube to draw a small volume of blood, and containers of a fixed volume of different liquids required to develop the test. Such liquids may include a sample dilution solution, a color developer, and a clarifying solution. The device and kit may provide instructions for the correct performance and sequencing of the solutions, and for interpretation of results.

Interpretation of the test results occurs in two steps. First, the user is instructed to check the presence of the first visual indicator, such as a change in color in procedural control. If the procedural control dot did not change color, the user is instructed to discard the rapid test device and treat test results as invalid. This may happen when an insufficient volume of collected fluid specimen is applied to the porous membrane or in other circumstances.

Once the first visual indicator for the procedural control is confirmed as positive by observing the change of its color, the user can then proceed to interpret the remaining dots on the porous membrane. A change in color of one or more of the remaining dots corresponding to certain recombinant antigen locations defines a second visual indicator configured to confirm the presence of the disease marker, whereby indicating a positive test result for a target disease. When no change in color is observed (negative second visual indicator), a conclusion of an absence of a target disease marker is made signifying a negative test result.

The direct flow rapid test device 10 of the type described above is advantageous for detecting the target disease for a number of reasons:
  it does not require a presence of a healthcare professional or a machine-conducted interpretation using a specialized reader or any medical equipment for obtaining test results. For this reason, it may be used not only by trained clinical personnel in a hospital or a laboratory but also by a minimally-trained medical personnel in the field, as well as self-administered by individual test subjects themselves;
  test results may be obtained faster than with other types of POC tests, such as lateral flow tests. In embodiments, the rapid test device 10 may be configured to deliver the test result in less than 5 minutes after application of the specimen fluid, such as in less than 4 minutes, less than 3 minutes, less than 2 minutes, or in about 1 minute from such specimen application. That compares favorably against 15-20 minutes required to obtain a reliable test result using a conventional lateral flow approach.

The expedient nature of the direct flow approach makes it easier for a single patient to test her/himself, or for a small number of clinical professionals to administer a large number of tests to a lot of subjects in a short amount of time. This not only allows testing for large groups of people by increasing the test throughput, but it also requires less training for the clinical personnel to counsel anxious subjects awaiting their test results. Because of their low complexity and simple execution, rapid POC tests can be widely disseminated through the population without the need for intervention of a formal health system. A parent may test her family members. A child may test his elderly relatives. POC tests may be particularly advantageous for performing surveillance of the target disease in rural areas and remote locations using a mobile clinic or a village distribution system. Another advantageous use of the higher throughput of this rapid test method is in airports, train stations or at large events—allowing screening of large number of people and providing a definitive result in a minimum amount of time.

Target Disease

One of the key objectives of the present invention is to facilitate collecting test information from a variety of test locations so as to create a detailed and up-to-date understanding of the spread of the target disease or condition. The term "target disease" as used in this description may include a broad number of infectious and chronic conditions where accurate epidemiologic surveillance may benefit society in general. Examples of the infectious disease or an analyte thereof include an adenovirus, *Bordella pertussis, Chlamydia pneumoniea, Chlamydia trachomatis*, Cholera Toxin, Cholera Toxin β, *Campylobacter jejuni*, SARS-CoV-2 (the virus causing Covid-19), Cytomegalovirus, Diptheria Toxin, Epstein-Barr NA, Epstein-Barr EA, Epstein-Barr VCA, *Helicobacter pylori*, Hepatitis B virus (HBV) Core, Hepatitis B virus (HBV) Envelope, Hepatitis B virus (HBV) Surface (Ay), Hepatitis C virus (HCV) Core, Hepatitis C virus (HCV) NS3, Hepatitis C virus (HCV) NS4, Hepatitis C virus (HCV) NS5, Hepatitis A, Hepatitis D, Hepatitis E virus (HEV) orf2 3 KD, Hepatitis E virus (HEV) orf2 6 KD, Hepatitis E virus (HEV) orf3 3 KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, *Leishmania donovani*, Lyme disease, MERS, Mumps, *M. pneumoniae, M. tuberculosis*, Parainfluenza 1, Parainfluenza 2, Parainfluenza 3, Polio Virus, Respiratory syncytial virus (RSV), Rubella, Rubeola, Streptolysin O, SARS, Tetanus Toxin, *T. pallidum* 15 kd, *T. pallidum* p47, *T. cruzi, Toxoplasma*, or *Vancella zoster*.

In other embodiments, the target disease is an infectious disease caused by or involving a microorganism, a pathogen, a microbe, a virus, a bacterium, an archaeum, a protozoan, a protist, a fungus, or a microscopic plant. The virus can be a SARS-CoV-2, influenza, or HIV. The bacterium can be *Mycobacterium tuberculosis*. The protozoan can be malaria.

When monitoring Covid-19 as the target disease, the rapid test of the invention may be configured to contain a recombinant antigen with an epitope specific for antibodies generated by a human subject who has been infected by SARS-CoV-2. The recombinant antigen is typically a single protein of SARS-CoV-2, a fragment (sub-unit) thereof, a modified or mutant version thereof, any of which may be glycosylated and further bio-modified as may be desired by the test kit designer. The recombinant antigen may include domains that are unrelated to virus but are useful for adapting the protein for use in the rapid test device. A recombinant antigen may be selected for binding with one of several individual SARS-CoV-2 antibody types, generally from the groups of IgG, IgM, and IgA antibodies. In embodiments, a recombinant antigen specific to SARS-CoV-2 IgM antibodies may be most useful for determining a recent infection as such may become undetectable weeks to months following the infection. In further embodiments, recombinant antigens specific to SARS-CoV-2 IgG antibodies may be used to detect prior infections as these antibodies may remain detectable for months or years, although it is known that antibodies sometimes disappear in as little as 60 days after infection. In further yet embodiments, recombinant antigens specific to SARS-CoV-2 IgA antibodies may be used to detect mucosal immunity to Covid-19—with the advantage that this antibody may be detected in mucous secretions like saliva in addition to blood.

In embodiments, further recombinant antigens may be used for the purposes of the present invention to detect neutralizing antibodies for Covid-19. Neutralizing antibodies are a very specific subset of antibodies that block a pathogen from being able to infect/enter a cell, thereby "neutralizing" their ability to be infectious. In general terms, that means that those particular proteins have some specific critical function in the pathogenesis cascade of events. For COVID-19, most neutralizing antibodies studied to date are those with affinity to parts of the so-called "spike" protein that are involved with binding the ACE2 receptor on epithelial cells. The scope of the present invention encompasses using epitopes for these neutralizing antibodies as part of the rapid test device.

Based on the instant disclosure, those skilled in the art are able to design a wide range of diagnostic kits and devices corresponding to the invention herein. One of the many uses of the first optical identifier is to distinguish the type of test being conducted. Currently, antibody diagnostics differ on a basic level among test manufacturers by targeting antibodies linked to different proteins found on or in the novel coronavirus, as described previously. For SARS-Cov-2 this can include the spike protein as a whole, or subunits thereof, including the receptor-binding domain (RBD) subunit, or alternatively the nucleocapsid protein.

Tests may be developed which further identify whether a subject is above a clinical threshold of neutralizing antibody sufficient to provide immunity to disease, or to prevent or reduce community spread. Reportedly, the US Centers for Disease Control and Prevention (CDC) and the EU's Joint Research Centre (JRC) are working with commercial entities to standardize international antibody tests for COVID-19. Such standards may, in theory, set quantitative levels of COVID-19 antibodies which are relevant for public policy (e.g. admission onto an airplane).

In a semi-quantitative embodiment, the device of the invention may provide a second visual indicator which identifies if a subject is above a set quantitative level of antibody, e.g. the second visual indicator is positive only if the patient is above the set level (not just the threshold level of detectability). Alternatively, the device may include a second visual indicator which is split into two domains, each of which indicates an increasing quantitative amount of antibody. A low level of antibody triggers only one of the domains, whereas the second domain requires a higher level of antibody that meets a selected pre-determined level. When it comes to reporting the test result via remote communication, the patient is invited to report how many of the second visual indicators are positive. Any reasonable number of domains may be employed as increasing quantitative levels for the second visual indicator. Thus, in certain embodiments, the device provided for use in the invention is semi-quantitative.

The first optical identifier may also include information on the specificity (% false positive) and sensitivity (% false negative) of the test performed to allow improved understanding of mass health surveillance testing.

The first optical identifier can be used to provide vital information quickly and directly to the central database of what standard has been tested, and what result was obtained. This standardization effort will impact global epidemiology efforts by enabling apples-to-apples comparisons, regardless of testing method, as well as to help measure the roll-out and effectiveness of potential vaccines across geographical regions.

In further yet embodiments, other recombinant antigens may be used to detect antibodies specific to a reaction to a certain vaccine such as Covid-19 vaccine, so as to distinguish it from antibodies arising naturally as a result of having the actual disease. This may be useful to better understand different types of immunity in a general population and track vaccine-mediated protection from natural protection, with follow-up implications for likely administration of a vaccine booster.

If more than one recombinant antigen is present in individually designated areas of the porous membrane of the rapid test device, any combination of the above-described recombinant antigens may be used.

In further embodiments, when two or more recombinant antigens are used, one of these recombinant antigens may be configured to have an epitope for a first target disease, for example, Covid-19, while the second recombinant antigen may be configured to have an epitope for a second disease, such as influenza. This may be useful in cases where the subject's symptoms are similar or common to both diseases and it is not clear how to differentiate them from each other otherwise.

When the target disease monitored by the invention is influenza, the disease marker may include hemagglutinin and/or neuraminidase. The hemagglutinin, in this case, may be selected from the group consisting of H1, H2, H3, H4, H5, H6, H7, H8, H9, H10, H11, H12, H13, H14, H15, and H16, and the neuraminidase may be selected from the group consisting of N1, N2, N3, N4, and N5.

In some embodiments, the disease marker may be a marker of inflammation, for example, a cytokine or a C-reactive protein. The marker of inflammation may also be IL-1β, IL-6, IL-8, IL-10, or TNFα.

In some embodiments, the disease marker is detected in a collected specimen of bodily fluid from the subject. Exemplary bodily fluids include without limitation blood, plasma, serum, sputum, urine, feces, semen, mucous, lymph, saliva, or nasal lavage as the invention is not limited in this regard.

Optical Identifier

FIG. 1 shows a first optical identifier 5 applied to the housing 4 of the rapid test 10. In embodiments, the first optical identifier may be one or several of the following: a unique numeric sequence, a unique alpha-numeric sequence, a one-dimensional barcode or a two-dimensional OR code, or an NFC tag.

Importantly, the presence of the first optical identifier 5 on the rapid test device 10 does not have any impact on the performance of the rapid test itself, and its use may occur after the test result is already obtained by the user. In that sense, adding the first optical identifier 5 provides an option for subsequent simplified and expedited reporting of the test results data but is not required per se to provide full benefits of the rapid test to the test subject.

For further clarity, the first optical identifier 5 on the rapid test device 10 does not include the name or personal identifier of the subject or any code or sequence that can be correlated with the subject's identity through a separate database. Rather, the first optical identifier provides information about the device or the kit, most importantly the disease being identified, and optionally including, but not limited to, its sensitivity and specificity, any threshold level of detection, its date of manufacture, and the supply chain by which it was provided to the location of the subject, as detailed further below. Different public health surveillance systems may include different types of information or higher or lower degrees of resolution of the supply chain, etc. in the central database (described below) which recognizes the first optical identifier upon receiving the communication.

In another aspect of the present invention, the remote communication of the test result may be conducted without identifying the test subject. Such de-identifying steps may be taken at the rapid test origin so that only de-identified information may be remotely communicated to the central database. In a simple embodiment, the remote communication of a test result may be communicated from a mobile device. While it may be possible to identify the owner or the user of the mobile device, it is not possible for the central database to identify with any certainty the subject who's test result is being communicated. The mobile device may belong to a friend, a parent, a child, a nurse or health authority official at the POC clinic where tests are being conducted. This may assure the test subject of preserving their privacy rights and not disclosing personal health information, which may be a subject of future leaks or database breaches. Such reassurance will further improve compliance with reporting the test results and improve the quality of epidemiologic surveillance using the methods of the present invention.

In another important aspect of the invention, the first optical identifier 5 may be configured by reading visually by the user of the test (in case of a unique numeric sequence or a unique alpha-numeric sequence) or by a machine optical reading using ubiquitous cameras of a smartphone, a laptop, a tablet, or a computer. In that case, there may be no requirement for using a specialized optical reader integrated into another medical apparatus. Thus, the first optical identifier avoids the need for complex reader technology and massively enhances the utility of the POC device or kit for epidemiological surveillance. In a manner of speaking, the device and/or kit according to the invention can be referred to as an "instrumented un-instrumented test".

The first optical identifier 5 may include a portion with an optical code for one or more messages pertaining to (i) the nature of the rapid test device, and/or (ii) the process of reporting the test result to the central database for epidemiologic surveillance of the target disease.

The first message or a group of messages coded in the first optical identifier may include one or more of the following:

- target disease identification information for the particular rapid test device
- the serial number of the rapid test device or a predefined batch of rapid test devices
- nature and/or location of the first visual indicator on the porous membrane 1 corresponding to the procedural control area
- presence and/or location of the second visual indicator defined by one or more areas containing respective recombinant antigens configured to detect the target disease marker
- date of manufacture of the rapid test device or a range of dates when the rapid device was manufactured (for example Q1 2020)
- the expiration date of the rapid test device
- expected geographical region or a country of distribution, shipping information relating to the location and supply chain delivery of the test device or kit. The second group of messages may include one or more of the following:
- a link to a secure website for reporting test results to the central database
- a prompt for downloading a smartphone or computer application configured to enter and transmit test results
- a link to instructions on how to perform the rapid test using the rapid test device 10,
- a prompt to use the location and timestamp of the host device to the optical reader used for reading the first optical identifier to supplement remote communication of the test results with the location of the rapid test and time of the rapid test
- a prompt to confirm delivery of the product to a customer within a predetermined geographical range of the sender
- a prompt to communicate rapid test validity using the first visual indicator
- a link to additional resources, support groups, and counseling for the target disease.

In embodiments, the first optical identifier 5 may comprise a positive optical identifier for communicating the positive test result and a negative optical identifier for communicating the negative test result. The user may be instructed to use either one code or another depending on the observation of the second visual indicator as described above.

Additional optical identifiers may be provided to report further information about the test subjects, such as demographics, presence of certain symptoms, a timeline of disease progression, etc. Additionally, it may include the location where the test was performed, or location information about the subject such as residency or range of recent travel. Such additional optical identifiers may be described in the instruction for use to make it more convenient for the test user to enter subject-related data into the reporting form for communicating to the central database.

In embodiments, such additional information may be selected from a group consisting of: (i) de-identified characteristic of the subject, (ii) de-identified history of prior testing of the subject for the target disease, and (iii) presence or absence of symptoms consistent with the target disease in the subject, as observed by the test user or reported by the test subject.

Numeric or Alphanumeric Codes

In its simplest form, the first optical identifier may be configured as a numerical or an alphanumerical sequence— unique to the particular rapid test device 10. Each number or a group of numbers and/or letters may be assigned to code one or more items from the first and/or the second groups of messages as described above. The user in this case does not have to have a smartphone or a computer to remotely communicate the test results. A simple text message may be sufficient for this purpose, for example by using Short Messaging Service (SMS texts). In further embodiments, a local telephone number or a toll-free telephone number may be provided for texting the numerical or alphanumerical code to remotely communicate the test result to the central database.

This way of communicating test results is easy and convenient and will not take much time or effort from the user—a key requirement to facilitate such remote communication. It may be advantageously deployed in developing countries, where communication technology is lacking modem sophistication prevalent in more developed countries. A simple cellular flip phone may be sufficient for this purpose.

In embodiments, remote communication of test results may occur over a single transmission, wherein the user sends a numerical code as described above. The time of transmission and/or the general geographical area of transmission may be automatically recorded by the central database and used as a time of the rapid test and the location of the rapid test.

In further embodiments, remote communication of the test results may occur over two or more transmissions in a two-way interactive mode of communication. In one example, the user may be first asked to send a code corresponding to the first optical identifier. Upon receipt of the code, the central database may be configured to (i) verify the validity of the transmission, and (ii) communicate back to the user with a greeting message and further instructions.

The step of verifying the validity of the transmission may be performed to check the code against one or more acceptance criteria including as examples:
  transmitted code is transmitted in full, it fits the designated code convention and is recognized by the central database
  this rapid test device did not reach the expiration date
  there is no active recall for this rapid test device
  this rapid test device was distributed in a region or a country sufficiently close to the area where the transmission has been sent from
  rapid test results for this rapid test device have not been already reported previously using the same first optical identifier,
  a history of rapid test sales or distribution corresponding to the rapid test is consistent with the first transmission.

Upon verifying the validity of the first transmission, the central database may be configured to generate a response message to the test user with suitable prompts to report the test result, as well as optionally to report the actual test time (which may precede the time of transmission), the actual test location (which may be different from the location of the transmission) as well as other de-identified subject information, for example, subject gender, age group or bracket, presence or absence of certain other diseases, conditions, or symptoms, etc. One example of such a communication scenario is shown in FIG. 2 illustrating successive screenshots of the user's phone two-way communication with the central database.

Figure 2:
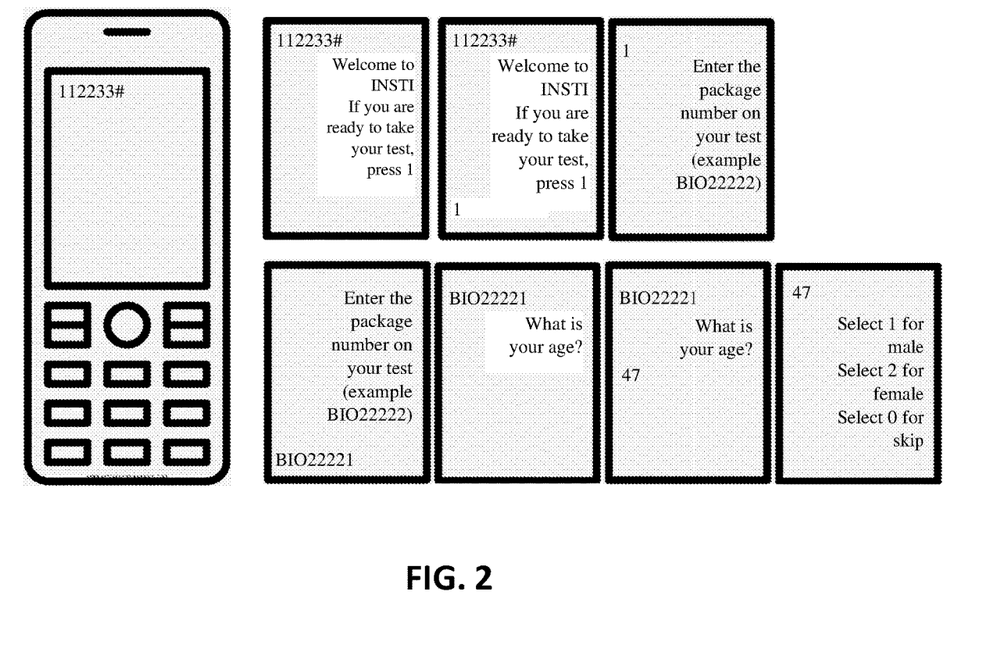
FIG. 2 is an exemplary scenario of two-way communication between the test user and the central database using text messaging.

While the actual test result may be transmitted to the central database after completion of the test itself, preliminary and subject data including demographics may be communicated prior to performing the rapid test itself as illustrated in FIG. 2. One advantage of this approach is providing the user with an option to review test instructions prior to initiating the test, which may be helpful for some subjects when self-applying the test procedure at home.

In other embodiments, to improve the security of data collection, a response message to the test user may further include instructions to use a different SMS address or a telephone number in order to communicate the actual test results. The central database may be configured to combine the test results communicated that way by the test user in a second transmission with the information about the rapid test device from the first transmission. This dual communication approach may further assure the security of the remote communication since intercepting of only one of the two transmissions may not provide adequate information to the unauthorized third party about the nature and results of the rapid test for the test subject.

Barcodes and QR Codes

The first optical identifier 5 may be presented on the rapid test device 10 as a barcode optically readable by conventional optical readers including cameras in smartphones, laptops, tablets, personal computers, and other small, portable, and hand-held electronic devices.

The barcode of the first optical identifier 5 may be a one-dimensional optical code or a two-dimensional optical code configured according to a variety of conventions developed for one- and two-dimensional optical codes that are well known in the industry. Optical codes used for the present invention may be black-and-white or colored codes as the invention is not limited in this regard.

The barcode may include the same information as described above for the numeric code. One advantage of using a barcode for reporting of test results is the convenience and speed with which the user with access to a smartphone or another modem electronic device may report the test result to the central database.

The optical barcode may be configured to prompt the electronic device of the user to either log-in to a secure website associated with the central database or to a location of the downloadable file containing a smartphone or computer software application dedicated to reporting the test results. Once the website or the application is accessed, the barcode may be further configured to populate the rapid test reporting form with the data characterizing the rapid test device. In addition, upon permission from the user, the barcode may be configured to automatically populate the test results form with the rapid test time and rapid test location extracted from the smartphone of the user. The user may be prompted to only enter the test result itself and submit the form for recording at the central database.

In further embodiments, after the rapid test is complete, the user may be prompted to first take a picture to include the image of the porous membrane and the first optical identifier. To facilitate this process, the first optical identifier may be located close to the porous membrane and in the same viewing field therewith so that a single image may be created recording both the first optical identifier and the results of the test.

Such image may then be processed by a smartphone or a computer using a dedicated application or program to automatically complete the following steps: (i) recognize the barcode in the image, and (ii) transmit the image along with the barcode to the central database, whereby automatically transmitting the rapid test result to the central database.

This approach has two advantages:
  it creates additional convenience for the user as the entire process is fully automated,
  it improves data integrity as the central database may be configured to automatically verify the test result using image recognition techniques and associate the test result with the specific barcode as well as the rapid test time and the rapid test location.

The central database may be further configured to store all transmissions for future audits and data integrity checks.

Near Field Communication (NFC) Tag

A functional alternative to the first optical identifier may involve using an NFC tag attached to the housing 4 of the rapid test device. Near Field Communication refers to a set of communication protocols for communication between two electronic devices over a distance of only about one and a half inch or less. This small distance advantageously excludes the NFC tag of the rapid test device from communicating with other smartphones that may be nearby. It offers a simple setup and can be used by a suitable smartphone to identify a particular rapid test device with a simple "tap". The structure of communication codes between the smartphone and the rapid test device may follow a similar convention as described in greater detail above.

In one use scenario, the smartphone of the healthcare worker may be used to quickly identify the rapid test device during use and prepopulate the form of the dedicated test results collection form with the information about the rapid test device.

Rapid Test Kit

Figure 3:
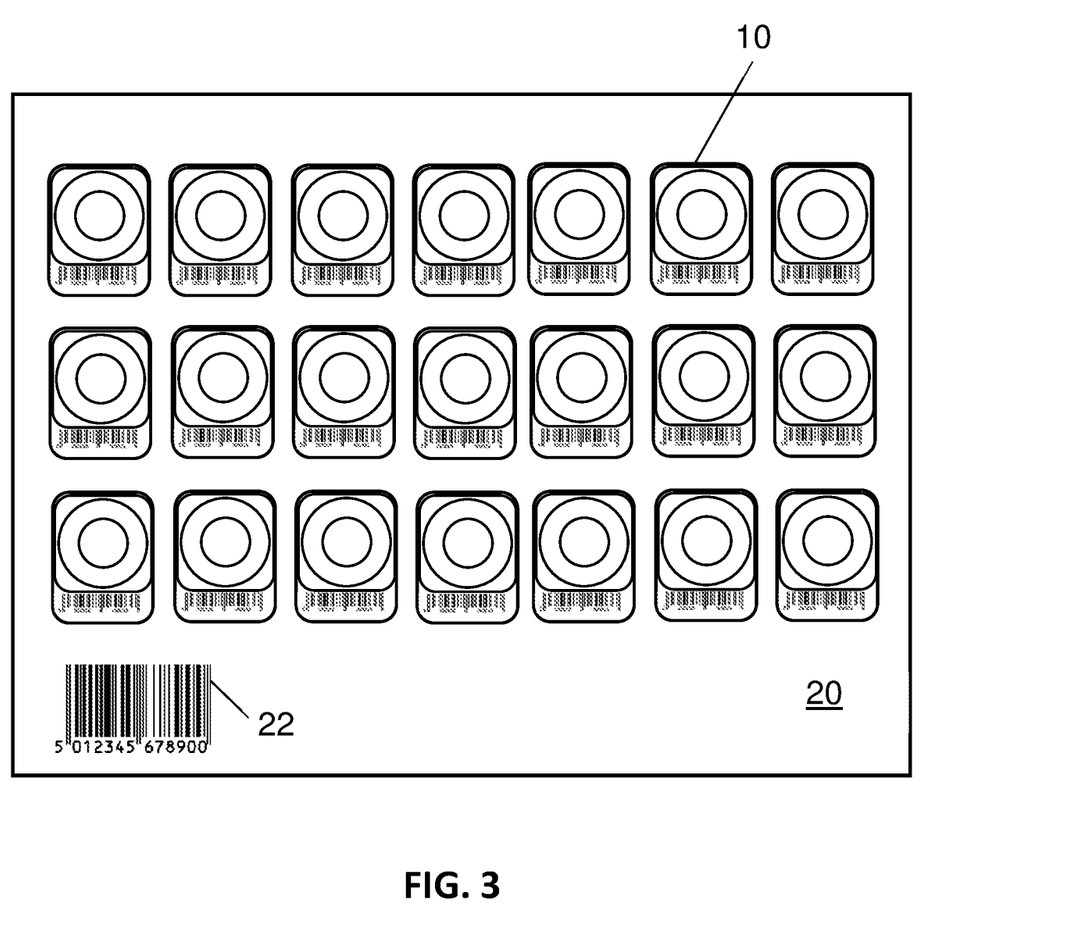
FIG. 3 is a schematic view of the rapid test kit including a plurality of the individual rapid test devices as in FIG. 1.

FIG. 3 shows a schematic of a rapid test kit 20 of the present invention. It may include one or a plurality of rapid test devices 10 as described above. In embodiments, 1, 2, 3, 4, 5, 10, 15, 20, 25, 30, 40, 50, 60, or more rapid test devices 10 may be included in a single rapid test kit 20 as the invention is not limited in this regard. The kit may be formed by a suitable enclosure or a package containing individual rapid test devices 10. The enclosure may also include instructions for use for the rapid test devices 10 as well as instructions for communicating the results of the rapid tests to the central database.

In embodiments, a second optical identifier 22 may be printed on or otherwise affixed to the rapid test kit. The second optical identifier 22 may be a unique numeric sequence, a unique alpha-numeric sequence, a one-dimensional barcode or a two-dimensional QR code, or an NFC tag. The type of the second optical identifier listed above may or may not be the same as that of the first optical identifier as the invention is not limited in this regard. In one example, the first optical identifier may be a numeric code, while the second optical identifier may be a barcode.

The second optical identifier 22 may be configured to contain information about the plurality of the rapid test devices 10 contained in the package. It may include one or more of the following information:

- target disease identification information for the particular rapid test kit
- range of serial numbers for enclosed rapid test devices or a single serial number for the entire batch of rapid test devices in the kit
- date of manufacture of rapid test devices or a range of dates when rapid devices were manufactured (for example Q1 2020)
- the expiration date of rapid test devices
- expected geographical region or a country of distribution.

In addition, the second optical identifier may include information about the use of rapid test devices and the reporting procedure for the test results. Examples of such information may include one or more of the following:

- a link to a secure website for reporting a plurality of test results to the central database, including at least some or all of the test results obtained using the rapid test devices contained in the kit
- a prompt for downloading a smartphone or computer application configured to enter and transmit some or all of the test results as a batch
- a link to instructions on how to perform the rapid test using rapid test devices 10,
- a prompt to use the location and timestamp of the host device to the optical reader used for reading the second optical identifier to supplement remote communication of the batch of the test results with the location of the rapid tests and time of the rapid tests.

One distinction between the first optical identifier and the second optical identifier may be in the structure of the coded information. The first optical identifier and the second optical identifier may be independently configured to facilitate remote communication of rapid test results obtained using individual rapid test devices to the central database for epidemiological surveillance of the target disease. The central database may be configured to identify any received transmission as that obtained with the first optical identifier associated with a single rapid test device or the second optical identifier associated with a batch or a plurality of individual rapid test devices from the kit.

The second optical identifier 22 may be configured for primary use by the healthcare worker administering a large number of tests, and not by an individual test subject performing a single rapid test. In embodiments, the second optical identifier may be scanned once to cause the opening of a website form or opening of a dedicated smartphone or computer software application or program configured for the rapid entry of a large number of individual test results. The time of the rapid test, the location of the rapid test and other pertinent information may be the same for all test result entries, which saves time for the healthcare worker by not having to enter this information multiple times for every rapid test that is performed using the same rapid test kit 20.

In further embodiments, both the rapid test kit 20 and the individual rapid test devices 10 may be equipped with a respective second optical identifier and first optical identifiers. This may be advantageous in circumstances where a healthcare worker may distribute some of the rapid test devices 10 for self-testing by individual subjects while using the remaining rapid test devices 10 for administering the test to other test subjects as a group.

In this embodiment, the central database may be configured to expect at least one, several, or all of the test results from individual rapid test devices 10 to be entered by the healthcare worker using the second optical identifier, while also vetting other incoming test results obtained from rapid test devices 10 coming from the same rapid test kit 20 for suitable correlation between the time and location of the individual rapid test devices 10 and the rapid test kit 20.

Central Database and Software

The present invention features a central database configured for accepting test results from a plurality of sources and using various communication routes, including the Internet (via encrypted cloud services), landline telephone lines, cellular networks, satellite networks, etc. The central database may be formed using a dedicated secure server configured to accept, verify, validate and store incoming test results along with test times and locations as well as additional de-identified information about test subjects, such as demographics of test subjects.

It may be further configured to allow generating one or more types of reports to disseminate the information—depending on the objectives of epidemiologic health surveillance requests. Multiple levels of data and reports access may be afforded to various customers depending on the access level assigned by the database administrator. As an example, the software of the central database may be configured to generate a geographical map of the distribution of the target disease using rapid test location and/or temporal distribution of the target disease using the time of rapid test administration. Once such reports are made available, an optimization of distributing healthcare resources and/or a vaccine for the target disease using data collected in the central database may be performed.

The central database may be adapted for interaction with test users via Web-enabled communication means such as a dedicated website containing web entry forms. The website may contain additional information such as instructions for use, helpful videos, support materials for dealing with a positive or negative test result, links to other resources for patients and healthcare professionals, entry forms for inquiring about health surveillance reports, etc.

As described above each discrete test result in the central database will have at a minimum the first optical identifier, including the test performed, the test result (positive or negative as the case may be), and date of entry of the communication. The location where the test was performed, if not provided directly by the communication, may be approximately located by extracting the sender's router IP address or cell-phone tower location based on the remote communication. The location of the test result sender may be further enhanced or confirmed if the first optical identifier is used by the manufacturer and supply chain entities to record the locations of delivery of the device or kit. For example, a regional health authority who purchases the kits for distribution could keep track of all the first optical identifier codes used in its region. They could then distinguish the remote communications received at the central database that correspond to their regional community. Or the manufacturer could provide supply chain information to health authorities, such as port of entry into a country, that corresponds to the first optical identifier. Downstream couriers could further record the location of distribution of the kits/devices at greater levels of resolution, including individual health regions, towns, cities or neighborhoods. The first optical identifier could be tracked by the supplier as closely as to specific pharmacies or clinics where the POC devices and kits are made available to individuals for testing.

Based on the current disclosure, those skilled in the art will have a wide range of tools available to use the test result data received in the central database for the central purpose of epidemiological surveillance of a target disease. Primarily, users will use the data to develop a geographical map of distribution of said target disease. Maps can be developed over time windows to identify the progress of the disease through a community. Serology tests such as described herein can be correlated with data from tests for active infections such as nucleic acid tests. Heat maps can be developed distinguishing uninfected populations from infected ones. Rate of increase of positive results in a region will be useful for identifying disease outbreaks and anticipating new ones. Disease distribution will also be useful for planning vaccine deployment into communities; or for identifying preferred locations for drug or vaccine clinical trials. More precise decisions can be made if the test result in the remote communication includes information such as demographics, presence of certain symptoms, a timeline of disease progression, etc, as described above.

In some cases, the data in the central database may be taken at face value. Alternatively, users may filter data. It is understood that persons who test negative are likely to return for testing until they eventually test positive (due to disease or vaccination). Thus, some people may record many tests, while others in the same community take no tests. Further, some tests may be reported inaccurately, or deliberately false. And certainly not all tests that are taken will be reported. Those skilled in the art of health surveillance understand how to filter spurious information that may distort findings. Primarily this is achieved by confirming observed results through local area re-testing and sampling strategies, by accepting a margin of error and by comparing data regions to similarly situated regions to identify grossly inconsistent data.

The inventors recognize that in certain embodiments, it may be desirable for a personal identifier to be linked to the test result. While this result is contrary to the main thrust of the invention due to the risk of privacy breach, it may be desirable for certain users that the remote communication to the central database be configured to support one or both individual as well as institutional membership. This will allow a member to easily track test results collected over time and produce reports reflecting such test history. Such reports may be instrumental to confirm a health status of an individual subject, such as a confirmation of being free from Covid-19, which may act as a "freedom pass" or "antibody passport" to enter the workforce, travel, or for other purposes. For institutional members, tracking and reporting on a record of test data entries may be useful for assessing the local rate of infection or for other purposes. Such embodiment is optionally achieved with a third optical identifier which identifies the test subject's name or other personal identifier, which may optionally be a secret code known only to the test subject. The subject identifier may be affixed at the location where the POC test is performed in the format of an additional optical identifier, or during the process of remote communication where the person's personal identifier is connected to the test result. For such personal identifiers, it is desirable for the epidemiological goals of the invention to employ a separate step which is clearly optional, at the user's discretion.

As an addition to the central database, a dedicated software application may be developed for operating on a user's computer, tablet, laptop, or smartphone as described above. The software application may be configured for recording pertinent test information and test result for a single test subject or a plurality of test subjects. The software application may be further configured to transmit test data immediately after its entry. In further embodiments, the software may be configured to transmit support information and link to additional resources upon receiving either a positive test result or a negative test result from a subject as appropriate.

In other embodiments, the software application may be configured to accumulate and store data from a number of test results for transmission at a later time. This may be done in case when reliable communication between the user and the central database is not available at the time when the tests are performed. In this case, the software application may be configured to first record actual test times and test locations, and then transmit that information as it is accumulated since a previous transmission. This approach may be used to avoid assigning a transmission time and transmission location to be the same as the respective rapid test time and rapid test location.

One use case of this feature may be for a mobile clinic traveling to remote regions without reliable internet or cellular connection. After performing a plurality of tests for a local population, the software application may be configured for recording all results while offline. Once at least one test result is entered offline, the software application may be configured to periodically seek to connect to the Internet (directly or using a Bluetooth or WiFi communication protocols) in order to transmit the test results to the central database. Once such a connection is re-established, rapid test results may be transmitted, verified, and accepted by the central database. After that is accomplished, the software application may be configured to reset the entry forms for future data entry.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for epidemiological surveillance of a target disease comprising the following steps:
   a. providing a rapid test kit comprising at least one rapid test device, said rapid test device in turn comprising:
      a porous membrane,
      a procedural control applied to said porous membrane, wherein the procedural control is configured to generate a first visual indicator to confirm a validity of test procedure,
      at least one recombinant antigen comprising at least one epitope for a disease marker corresponding to said target disease, said at least one recombinant antigen applied to said porous membrane to capture antibodies specific to said disease marker from a single collected specimen, wherein said at least one recombinant antigen forming a second visual indicator configured to confirm if said disease marker is present in said collected specimen,
      said rapid test kit further comprising a first optical identifier provided therewith and applied to either said rapid test kit or said rapid test device, said entire first optical identifier is fully visible on said rapid test kit, b. collecting said single specimen from a subject and applying said single specimen to said porous membrane, c. visually confirming rapid test validity using said first visual indicator, d. visually detecting a test result using said second visual indicator including a presence (positive test result) or an absence (negative test result) of said target disease marker in said subject, wherein said test result is obtained without using said first optical identifier, and e. after performing said rapid test, using said first optical identifier to remotely and anonymously communicate said visually detected test result to a central database configured for epidemiological surveillance of said target disease, wherein said remote communicating further permits identifying a time of said rapid test and a geographical location of said rapid test.

2. The method as in claim 1, wherein said step (e) further comprising communicating results of confirming rapid test validity from step (c).

3. The method as in claim 1, wherein said rapid test kit comprising a plurality of said rapid test devices, said rapid test kit further comprising a second optical identifier, said step (e) further comprising communicating said second optical identifier to said central database, whereby associating a single test geographical location and a single time of test with a plurality of rapid test results obtained using said plurality of rapid test devices from said rapid test kit, wherein said test geographical location and time of test are entered once for all of the individual test results entered therewith.

4. The method as in claim 3, wherein said step (e) is performed using said first optical identifiers to report rapid test results using individual rapid test devices and/or said step (e) is performed using said second optical identifier for a batch of rapid tests performed at the same geographical location and at the same time.

5. The method as in claim 1, wherein said steps (c) and (d) are performed without a need for neither a professional interpretation nor a machine-conducted interpretation.

6. The method as in claim 1, wherein said rapid test device is a direct flow rapid test device.

7. The method as in claim 1, wherein said step (c) or said step (d) are performed within 5 minutes after applying said collected specimen onto said porous membrane.

8. The method as in claim 1, wherein said step (e) further including a step of remotely communicating said test result using a telephone connection, a cellular connection, a WiFi connection, a Bluetooth connection, or over the Internet.

9. The method as in claim 1, wherein in said step (a) said first optical identifier is a unique numeric sequence, a unique alpha-numeric sequence, or a one-dimensional barcode.

10. The method as in claim 1, wherein in said step (a) said first optical identifier comprises a positive optical identifier for communicating said positive test result and a negative optical identifier for communicating said negative test result.

11. The method as in claim 3, wherein said step (a) further including providing one or more additional optical identifiers to be used in place of said first optical identifier or said second optical identifier in order to remotely communicate said test result along with additional information about said subject.

12. The method as in claim 11, wherein said additional information is selected from a group consisting of: (i) de-identified characteristic of the subject, (ii) de-identified history of prior testing of the subject for said target disease, and (iii) presence or absence of symptoms consistent with said target disease in the subject.

13. The method as in claim 1, wherein said step (e) further including a step of storing said test result when remote communication to said central database is unavailable, said test geographical location, and said time of test, followed by communicating thereof to said central database at a later time when remote communication to said central database is reestablished.

14. The method as in claim 1, wherein said step (e) further comprising a step of verifying a validity of said test results against an acceptance criterion.

15. The method as in claim 14, wherein said acceptance criterion is selected from a group comprising: (i) a geographical record of rapid test regional distribution corresponding to said geographical location of the test, (ii) a history of rapid test deployments corresponding to said rapid test time, and (iii) absence of a previous test result reporting based on the same first optical identifier.

16. The method as in claim 1, wherein said step (e) further comprising acquiring an image of said porous membrane together with said first optical identifier and transmitting thereof to said central database for subsequent automated processing using an image recognition technique.

17. The method as in claim 1, wherein said step (e) further comprising a step of generating a geographical map of distribution of said target disease using said rapid test geographical location and/or a temporal distribution of said target disease using said rapid test time.

18. The method as in claim 1 further comprising a step (f) of distributing healthcare resources and/or a vaccine for the target disease using data collected in said central database.

19. The method as in claim 1, wherein in said step (a) said second visual indicator is formed using a plurality of individual epitopes or subsets of epitopes for at least one disease marker corresponding to said target disease.

20. The method as in claim 1, wherein in said step (a) said second visual indicator is separated into two or more domains, with each domain corresponding to a different quantitative level of disease marker present in the sample.

21. The method as in claim 1, wherein said step (e) of remotely communicating said test results further comprising a step of de-identifying the subject prior to said remote communication.

22. The method as in claim 1, wherein said first optical identifier does not identify the subject personally either directly or by inference through a source database.

23. The method as in claim 1, wherein in said step (a) said first optical identifier is a two-dimensional QR code.

24. In combination, a rapid test device comprising a first optical identifier and a central database, both the rapid test device and the central database are respectfully configured for use in the method of claim 1.

25. The rapid test kit as in claim 24, wherein said target disease is Covid-19.

26. In combination, a rapid test kit comprising a first optical identifier a central database, both the rapid test device and the central database are respectfully configured for use in the method of claim 1.

* * * * *